United States Patent [19]

Balkovec et al.

[11] Patent Number: 5,233,023
[45] Date of Patent: Aug. 3, 1993

[54] PROCESS FOR PHOSPHATE ESTER COMPOUNDS OF CERTAIN CYCLOHEXAPEPTIDES

[75] Inventors: James M. Balkovec, North Plainfield; Mallory F. Loewe, Marlboro; David J. Mathre, Skillman, all of N.J.

[73] Assignee: Merck & Co., Inc., Rahway, N.J.

[21] Appl. No.: 738,058

[22] Filed: Jul. 30, 1991

[51] Int. Cl.$^5$ .................. C07K 1/02; C07K 1/06; C07K 7/50
[52] U.S. Cl. .................... 530/317; 530/345
[58] Field of Search ............... 514/7; 530/317, 321, 530/345

[56] References Cited

U.S. PATENT DOCUMENTS 5,021,341  6/1991  Giacobbe et al. ............... 435/71.1

OTHER PUBLICATIONS

Khorana, H. G. et al., J. Chem. Soc. 1953, pp. 2257–2260.
Boehm, M. F. et al., Tetrahedron Letters, 29 (41), 5217–5220 (1988).

Primary Examiner—Jeffrey E. Russel
Attorney, Agent, or Firm—Alice O. Robertson; Raymond M. Speer

[57] ABSTRACT

A facile process for preparing a compound of the formula

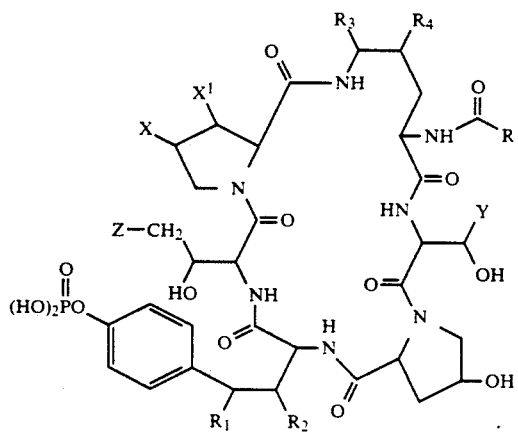

or a salt thereof, wherein R, $R_1$, $R_2$, $R_3$, $R_4$, X, $X^1$ Y and Z are as defined in the specification, by direct phosphorylation of the corresponding phenolic compound with tetrabenzyl pyrophosphate in the presence of lithium hydroxide is described.

4 Claims, No Drawings

PROCESS FOR PHOSPHATE ESTER COMPOUNDS OF CERTAIN CYCLOHEXAPEPTIDES

The present invention is directed to a facile process for preparing phosphate ester compounds of certain cyclohexapeptides by direct phosphorylation.

BACKGROUND OF THE INVENTION

Compound IA, which is described and claimed in copending application Ser. No. 07/495,199 and having the formula (IA) (SEQ ID NO:1)

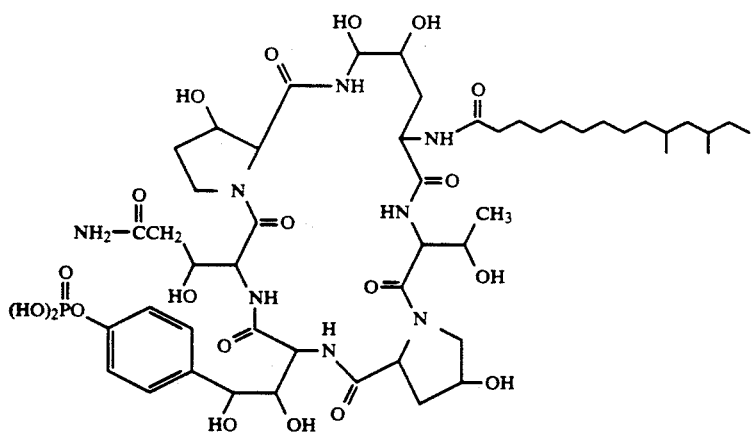

is a phosphorylated derivative of a natural product which is useful for the control of certain fungi and also for the control of parasitic *Pneumocystis carinii* as subsequently described.

The natural product from which Compound IA is derived is produced under certain conditions on the cultivation of *Zalerion arboricola* ATCC 20957 and may be represented by formula (A) (hereinafter Compound A; SEQ ID NO:1).

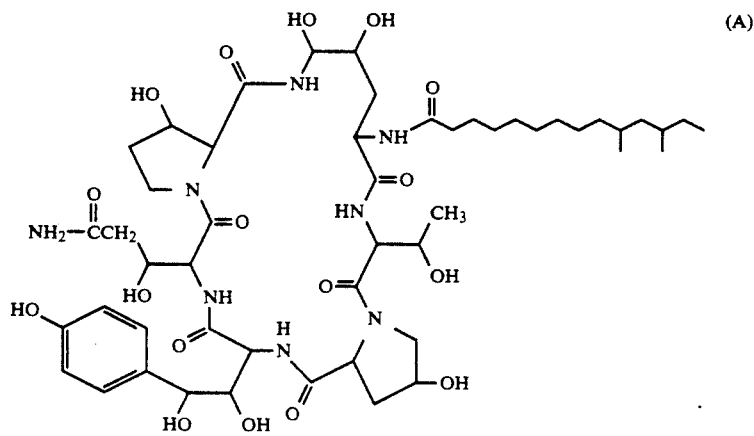

Compound A has a base-sensitive hydroxyl group in the 5-position of the ornithine component of the cyclopeptide, hence, in the normally preferred procedure for ester formation, the hydroxyl in the 5 position has been protected with benzyl ether formation followed by reaction elsewhere. Thus, the compound of formula (IA) (SEQ ID NO:1) has been prepared by forming the benzyl ether (SEQ ID NO:1), followed by phosphorylation to form a dibenzyl phosphate (SEQ ID NO:1), then hydrogenolysis to remove the benzyl groups from the phosphate, according to the following sequence of reactions.

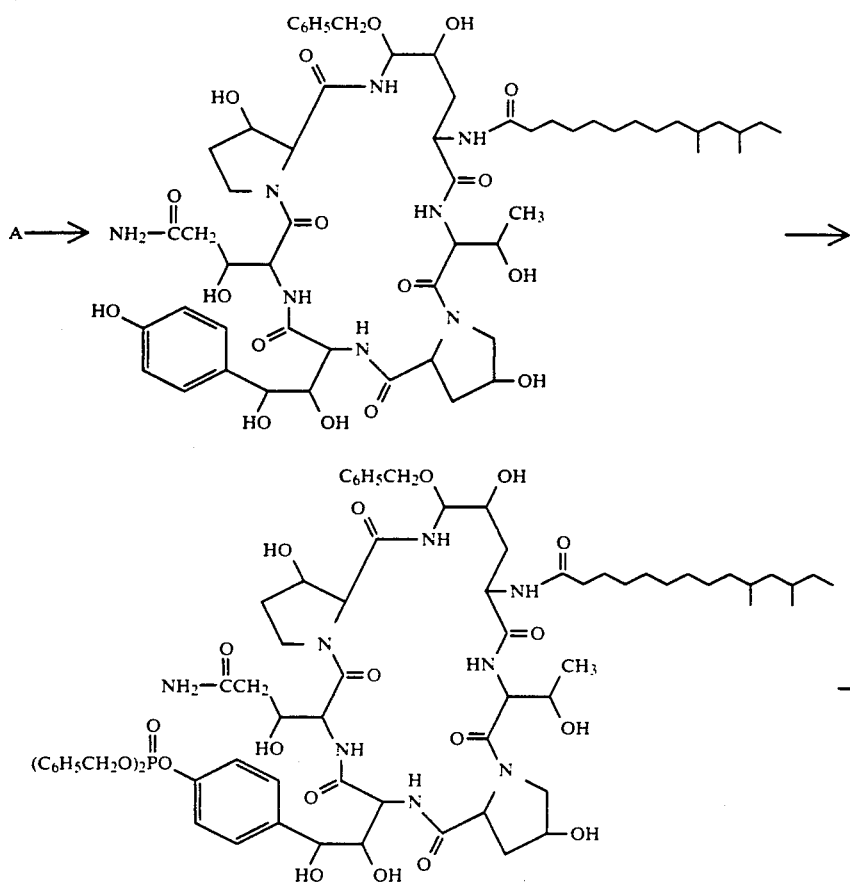

STATEMENT OF THE INVENTION

According to the present invention, it has been discovered that Compound X (SEQ ID NOS: 1-17) having the formula

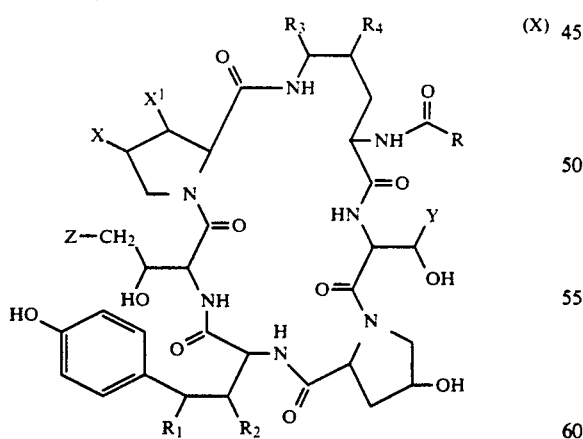

wherein the substituents are as hereinafter described, and of which Compound A is a species, may be directly phosphorylated without the need to protect the 5-position of the ornithine to obtain a dibenzyl phosphate which is then subjected to hydrogenolysis to obtain the phosphate ester (I) (SEQ ID NOS: 1-17) having the formula

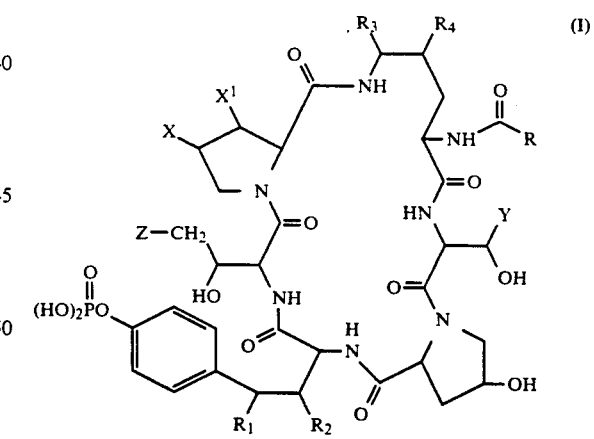

and when the starting material is Compound A to obtain Compound IA. In formulas I and X, the substituent may be defined as follows:

R is $C_{13}$-$C_{17}$ alkyl, $C_{13}$-$C_{17}$ alkenyl, $C_{13}$-$C_{17}$ alkynyl, phenyl and phenyl substituted with $C_1$-$C_{10}$ alkyl, $C_1$-$C_{10}$ alkoxy, $C_1$-$C_{10}$ alkylthio or $C_1$-$C_{10}$ alkylamino;

$R_1$, $R_2$, $R_3$ and $R_4$ are independently H or OH;

X is H, OH or $CH_3$ $X^1$ is H or OH,

Y is H or $CH_3$

Z is H or —$CONH_2$ provided that at least one of X and $X^1$ is OH.

There is also described a process which permits isolation of Compound I as a crystalline potassium salt and its conversion to other salts. The salt form of Compound IA may be represented by formula (IB) (SEQ ID NO:1)

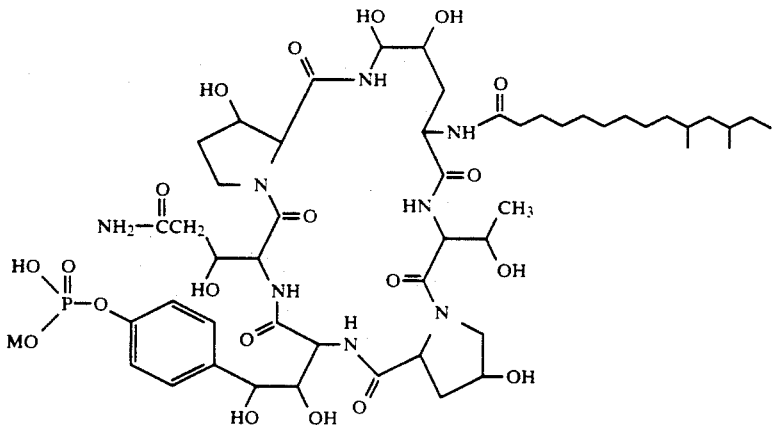

(IB)

wherein M is a cation forming salt group.

By "cation forming salt group" is meant groups as potassium, sodium, rubidium, cesium, lithium, magnesium, calcium, ammonium and quaternary ammonium.

DESCRIPTION OF THE INVENTION

The process of the present invention for facilely producing Compound I or IA comprises (1) intimately mixing Compound X or A with tetrabenzyl pyrophosphate in the presence of lithium hydroxide to obtain a dibenzyl phosphate ester, and (2) debenzylating by hydrogenolysis on palladium on carbon.

The first step in the process of the present invention is intimately mixing Compound A with tetrabenzyl pyrophosphate in the presence of lithium hydroxide to obtain the dibenzyl phosphate of Compound A. Although the reaction may be carried out employing solid lithium hydroxide, in the most facile process of the present invention, the reaction is carried out so that at the time of the reaction all reactants are present in solution.

Compound A may be added as a solid to the solvent system containing the phosphorylating agent and dissolving it therein before the other reactants are added.

Tetrabenzyl pyrophosphate is the phosphorylating agent. Although other activated phosphorylating agents may be employed, this is the preferred phosphorylating agent. Tetrabenzyl pyrophosphate may be prepared by a known procedure ahead of time; it is, however, preferable to prepare it just prior to use as a step in the overall process as subsequently described.

The lithium hydroxide is employed as an aqueous solution, preferably a 2M solution, although 1.0 to 2.5M may be employed. The amount of lithium hydroxide which is added must be carefully controlled. It is critical that the amount be substantially equivalent, optimally 1.05 equivalents. Overcharging the lithium hydroxide results in substantial product loss because of base catalyzed decomposition. Undercharging will cause incomplete reaction which, however, can be remedied by very careful addition of the base with scrupulous HPLC monitoring.

The reaction medium for the phosphorylation is preferably dimethylformamide which is a solvent for the reactants and which is miscible with the aqueous base. The quality of the dimethylformamide should be that which assays for water $\leq 50$ $\mu$g/mL and dimethylamine $\leq 100$ $\mu$g/mL.

The temperature for carrying out the reaction is critical. It should not deviate much from the $-15°$ C., i.e., about $-13°$ to $-17°$ C. An increase in temperature to $-10°$ C. will result in a 2.5 percent yield loss, and an increase to $0°$ C., a 5 percent yield loss.

The phosphorylation reaction is hereinafter described in terms of Compound A as starting material for convenience but is to be understood the process applies to use of X as starting material.

The phosphorylation reaction is carried out by adding Compound A (1 equivalent) to a well-agitated dimethylformamide solution containing 1.15 equivalents of tetrabenzyl pyrophosphate and sufficient additional dimethylformamide added to provide 6 milliliters (mL) per gram of Compound A. After complete dissolution of Compound A, the solution is cooled to $-15°$ C. An aqueous solution of lithium hydroxide (titrated just before use) is added at a rate to maintain the internal temperature at $-15°$ C. After completion of the addition, the mixture is allowed to stand for 1 to 3 hours at $-15°$ C. until the reaction is complete (as determined by HPLC) with the formation of the dibenzyl phosphate of Compound A.

In the preferred process, the tetrabenzyl pyrophosphate is prepared as the first step so that it may be maintained in solution without isolation. It is prepared by the dehydration of dibenzylphosphoric acid with dicyclohexylcarbodiimide, then separating from the dicyclohexylurea by-product.

It is important that dibenzylphosphoric acid be of good purity. The purity of it has a pronounced effect on the yield, purity and stability of tetrabenzyl pyrophosphate. The purity of dibenzylphosphoric acid should be about 98–99 percent as determined by titration, HPLC and NMR.

The tetrabenzyl pyrophosphate, if not immediately used, must be stored with protection against moisture. The solution stability of tetrabenzyl pyrophosphate depends on the solvent and the moisture content of the solvent. In solvents such as ethyl acetate, dimethylformamide and t-butyl methyl ether, the tetrabenzyl pyrophosphate decomposes at a rate of about 1 percent per day irrespective of low water content, and more rapidly when the water content is $\geq 100$ $\mu$g/mL. However, in tetrahydrofuran at about $0°$ C. with the water content ≦100 μg/mL the loss is ≦0.5 percent per week. Thus, the preparation of tetrabenzyl pyrophosphate is carried out in tetrahydrofuran. However, the water content of the tetrahydrofuran should be ≦50 μg/mL.

For the preparation of tetrabenzyl pyrophosphate, about 1.05 moles of dicyclohexylcarbodiimide is used for 2 moles of dibenzylphosphoric acid.

In carrying out the preparation of tetrabenzyl pyrophosphate, a solution of dicyclohexylcarbodiimide in tetrahydrofuran is added to a solution of dibenzylphosphoric acid in tetrahydrofuran at 20°-25° C. and the mixture stirred at this temperature for 1 to 3 hours until the reaction is complete with the formation of tetrabenzyl pyrophosphate and the dicyclohexylurea by-product. The latter is removed by filtration and the resulting tetrabenzyl pyrophosphate solution stored at 0° C. with protection from moisture.

While tetrahydrofuran is the solvent for the preparation of tetrabenzyl pyrophosphate, dimethylformamide is the preferred solvent in the phosphorylation reaction. Thus, when the phosphorylation step is ready to be performed, a solvent replacement is first carried out. For this replacement, tetrabenzyl pyrophosphate solution is diluted with dimethylformamide (water content ≦50 mg/mL, dimethylamine ≦100 mg/mL) and the tetrahydrofuran removed in vacuo (100 mBar) while the temperature is maintained below 30° C. to minimize disproportionation of tetrabenzyl pyrophosphate. The amount of dimethylformamide added should be less than 50 percent of the amount calculated to be employed in the phosphorylation reaction. The dimethylformamide solvent is dried over 13×molecular sieves to remove both water and dimethylamine before use in this step.

The dibenzyl phosphate of Compound A which is obtained in the phosphorylation reaction is then subjected to hydrogenation to remove the benzyl groups. The reaction mixture in the phosphorylation is in dimethylformamide. For hydrogenation, the desired solvent is ethanol/water. While the dibenzyl phosphate may be recovered by removing the solvent and the phosphate then dissolved in the ethanol/water medium, according to the process of the present invention the dibenzyl phosphate may be prepared for hydrogenation without isolation. This may be carried out by first effecting a solvent transfer.

The solvent transfer may be carried out by first acidifying the phosphorylation reaction mixture to neutralize the lithium hydroxide, then diluting the reaction mixture into 50:50 (v/v) ethanol/water, passing the diluted solution through a non-functionalized resin column wherein the dibenzyl phosphate ester is strongly adsorbed on the resin, then washing the column with 50:50 ethanol/water to remove the dimethylformamide and by-product lithium dibenzyl phosphate, and finally eluting the dibenzyl phosphate ester with 90:10 ethanol/water. The solution is then used directly for the hydrogenolysis (debenzylation) step. The dilution of the dimethylformamide is into a large excess of 50:50 ethanol/water. About 10 volumes are appropriate. It is very important that the dimethylformamide solution is diluted into the ethanol/water. The inverse mode results in a gummy material. Also, it is important that once the solution has been diluted that the column be run as quickly as possible to avoid hydrolysis of the ester desired to be retained on the column.

Suitable resins for the solvent transfer include "AMBERCHROM" CG-161 md (50-100 μm) and "AMBERCHROM" CG-161 cd (80-160 μm). ("AMBERCHROM", trademark of Rohm & Haas, is a divinylbenzenepolystryrene resin available from Toso-Haas). Other non-functionalized resins may be employed. By "non-functionalized resins" is meant an adsorbing resin which does not have a functional group. Thus, other column resins of divinylbenzene-styrene copolymer type would be suitable. Prior to use the resins must be prepared. The preparation of the resin and the regeneration thereof are subsequently described.

The eluted fractions containing the dibenzyl phosphate ester are subjected to catalytic reduction. Palladium on carbon is the preferred reduction catalyst. A pressure of about 2.5 to 3.5 atmospheres of hydrogen, preferably 3 atmospheres, is suitable and is carried out for a period of time which varies with the loading of Pd/C to obtain the desired Compound I in the acid form. After completion of the reduction, the catalyst is removed by filtration and the solution of the acid product if not immediately isolated is maintained at −10° C.

The free acid may be isolated by conventional mean but is preferably converted directly from the filtrate solution from the hydrogenolysis to a mono salt. Although salts may be made in this way of various alkali metals, or calcium, magnesium, ammonium or quaternary ammonium, the mono-potassium salt has been found to be the one most consistently obtainable in crystalline form by the direct conversion and is therefore the preferred salt to which acid is converted for isolation.

The process for direct conversion to the mono-potassium salt is carried out by adding water to the filtrate and neutralizing by the cautious addition of exactly one equivalent of 1.0M aqueous potassium hydroxide at 20°-25° C. The amount of water added is such that the total water content at the end the neutralization is 20 percent. The mixture is then warmed to 50°-60° C., seeded, and ethanol slowly added until the water content is 13-15 percent and the resulting mixture aged for about 1 hour at about 50°-60° C., then allowed to cool slowly to 20°-25° C. over a 12 to 18 hour period to form crystals. The crude crystalline material is recovered by filtration.

The crude solid is then purified by either using a "hot-swish" (warm wash) procedure or a recrystallization procedure. The "hot-swish" procedure is carried out by suspending crude solid in 80:20 (v/v) ethanol/water, about 10 milliliters per gram of solid, and the mixture heated to 50°-60° C. and stirred for 1-3 hours at this temperature, then allowed to cool slowly to 20°-25° C. over a 12 to 18 hour period to obtain purified crystals.

Alternatively, the crude crystals may be recrystallized by dissolving the crude solid in 50:50 (v/v) ethanol/water, about 12 milliliters per gram of solid at about 75°-78° C. and thereafter adding absolute ethanol over a 0.5 to 1.0 hour period. About 18 milliliters of solvent per gram of product is satisfactory. The mixture then is cooled somewhat, to 70°-75° C., seeded, and then slowly allowed to cool to 20°-25° C. over a 12 to 18 hour period to obtain the purified crystalline mono-potassium salt product.

The purified product from either procedure is isolated by filtration and the wet cake sequentially washed with 85:15 ethanol/water, 90:10 ethanol/water, 100 percent ethanol, and hexane. A stream of nitrogen or dry air is drawn through the cake for 12 to 48 hours at 20°–25° C. to dry the product. The drying procedure is necessary to reduce the ethanol content to ≦0.5 weight percent. Vacuum drying at ambient temperature does not adequately remove the ethanol and at elevated temperature causes decomposition. After isolation, the product is stored at <−20° C.

When other salts are desired, as an alternative procedure the mono-potassium salt may be converted to another salt by the following general procedure wherein the mono-potassium salt in water, 80:20 water/ethanol, or 80:20 water/acetonitrile is adsorbed onto a resin column preferably AMBERCHROM 161. The column is then washed with two bed volumes of 0.1 M'$H_2PO_4$ in water or 80:20 water/ethanol where M' is the desired cation. If necessary, the pH of this solution is adjusted to 4.5. The column is then washed with two bed volumes of water or 80:20 water/ethanol to remove the excess salts. The product, as the mono-cation salt is eluted from the column with 20:80 water/ethanol. The rich fractions containing the product are combined and concentrated in vacuo. The residual water may be removed by either azeotropic distillation with ethanol or by lyophilization. Depending on the cation, the salt may be purified by crystallization.

Other methods known to the skilled in the art for conversion or isolation also may be employed.

The following examples illustrate the invention but is not construed to be limiting:

EXAMPLE 1

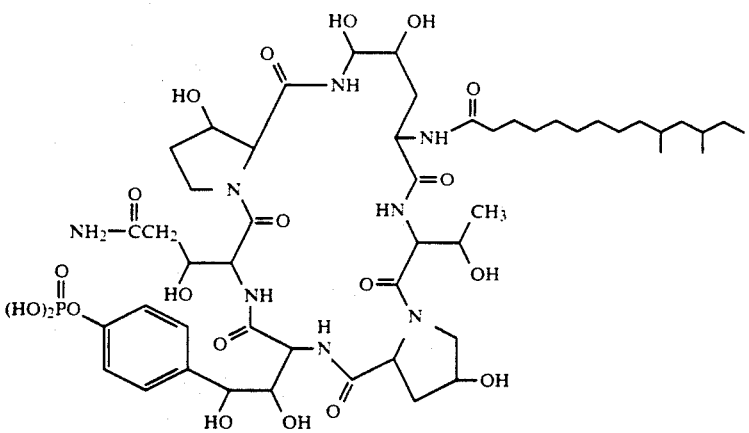

Preparation of Tetrabenzyl Pyrophosphate

A flask fitted with a nitrogen inlet, overhead stirrer, teflon-coated thermocouple probe, and pressure-equalizing addition funnel was charged with 350 milliliters of dry (water content ≦50 μg/mL), peroxide-free tetrahydrofuran, followed by 50.0 grams (174 millimoles) of dibenzylphosphoric acid (DBP), and the resulting mixture was stirred until the solid dissolved (about 10-15 minutes). A solution of 18.9 grams (91.6 millimoles) of dicyclohexylcarbodiimide (DCC) in 215 milliliters of THF was added from the addition funnel to a stirred, cooled (water-bath) solution of DBP at a rate to maintain the temperature at about 20°–25° C. The reaction is slightly exothermic and the addition took about 30 minutes. Within minutes, a precipitate of dicyclohexylurea formed in the mixture. Stirring was continued for about 2 hours at 20°–25° C. The reaction was monitored by HPLC assay using VYDAC C-18 (300A, 4.6×250 mm) column with water (0.02M $KH_2PO_4$) acetonitrile as eluent. The reaction was complete in about 1 hour (assay showing <2 percent unreacted DBP). The mixture was then filtered while excluding moisture to remove dicyclohexylurea. The filter cake was washed with two 25 milliliter portions of THF. The solution when assayed by HPLC showed 45.9 grams (98 percent) yield of tetrabenzyl pyrophosphate (TBPP) in 620 milliliters of THF (0.137M). The filtrate was then stored at 0° C. with exclusion of moisture until the next step.

Phosphorylation

A flask fitted with a nitrogen inlet, overhead stirrer, and teflon coated thermocouple probe was charged with 293 milliliters of the 0.127M TBPP solution (40.1 mmol) and 120 milliliters of dried (over 13×molecular sieves) DMF. The mixture was then concentrated in vacuo (100 mBar) at 25° C. to a volume of about 140 milliliters.

In a separate vessel, 40.0 grams (37.2 grams adjusted for 7.1 percent water content, 34.9 millimoles) of Compound A was added portionwise to 120 milliliters of DMF. The resulting mixture was stirred at ambient temperature until all the solid dissolved. This solution of Compound A was added to the TBPP solution and the mixture cooled to −15° C. 18.7 milliliters of 1.95M lithium hydroxide (36.6 mmol) was added dropwise over 0.5 to 1 hour to a well-stirred reaction mixture. The rate of addition and external cooling was adjusted to maintain the internal temperature at −15° C. After completion of the addition, the mixture was stirred for 3 hours at −15° C. The progress of the reaction may be

SEQ ID NO: 1 monitored by HPLC using "ZORBAX" C8 (Dupont) column (4.6×250 mm) using 1:1 acetonitrile/water (0.02M $KH_2PO_4$). After completion of the reaction, the solution is allowed to warm to ambient temperature. Using the same assay method, the yield amounted to 39.1 grams.

Solvent Exchange

A. Preparation of the Resin Column 100 grams of "AMBERCHROM" CG-161 (medium diameter) was added to a gently agitated solution of 80:20 (v/v) acetone/water and the mixture stirred gently for 4 to 12 hours at room temperature. The mixture was slurry packed onto a 4.3×30 cm. adjustable bed column. The resin was then washed with acetone. The wash was continued until low molecular weight aromatics were no longer detected in the eluate. (A capillary gas chromatographic assay using a DB-1

(J&W Associates) column was employed to analyzed the eluate.) The column then was washed with 1.5 liters of 100 percent ethanol at 20 mL/min and then with 1.5 liters of 50:50 (v/v) ethanol/water.

B. Replacement of Solvent 9.7 grams (162 mmol) of acetic acid was added to 330 milliliters of the phosphorylation mixture containing Compound B (assay 38.5 g, 29.1 mmol) at 20°-25° C. The mixture was stirred for 15 minutes and then diluted into 2.6 liters of a well-agitated solution of 50:50 (v/v) ethanol/water.

The diluted phosphorylation reaction mixture was loaded onto the "AMBERCHROM" resin column at a rate of 20 mL/min, and 140 milliliter fractions collected. (The column was monitored by HPLC assay on "ZORBAX" C8 column with 45:55 water (0.02M $KH_2PO_4$)/acetonitrile with detection at 210 nm.) The column was then washed with about 1.5 liters of 50:50 (v/v) ethanol/water to remove the dimethylformamide and dibenzyl phosphate.

Compound B was then eluted with 1.5 liters of 90:10 (v/v) ethanol/water at 20 mL/min and 140 milliliter fractions were collected. The fractions which were determined to contain more than 3 g/L were combined and found to amount to a yield of 38.5 grams.

The solution was stored at 0° C. while awaiting hydrogenolysis.

Hydrogenolysis

Under an atmosphere of nitrogen, 2.4 grams (5 weight percent) of Pd/C was added to 775 milliliters of about 90:10 ethanol/water solution containing 38.5 grams (29.1 mmol) of Compound B in a vessel previously purged with nitrogen. The mixture was hydrogenated at 40 psi for about 2 hours at 20°-25° C. until completion of the expected hydrogen uptake. Upon completion of the reaction, the vessel was vented and flushed with nitrogen. The reaction mixture was filtered through a pad of prewashed (90:10 ethanol/water) "SOLKA-FLOC" (cellulose based filter aid, James River Corp. of Virginia) and the filter cake washed twice with 25 milliliter portions of 90:10 ethanol/water. The solution was assayed both by HPLC and titration for acid product. The yield was found to be 32.2 grams.

Neutralization/Crystallization

Compound IA obtained by a series of reactions carried out in a manner similar to that above described was isolated and purified to a crystalline salt in the following manner:

To a stirred solution of 1.67 liters of a filtered hydrogenation mixture containing 58.5 millimoles of Compound IA as free acid and 200 milliliters of water, was added 109 milliliters of water at 20°-25° C. to bring the water content of the mixture to 20 percent. While stirring was continued, 58.5 milliliters of 1M aqueous potassium hydroxide was added dropwise over a 1 hour period whereupon the monopotassium salt began to crystallize. The addition funnel was washed twice into the mixture with 20 milliliters of ethanol. The stirred mixture was warmed to 60°-65° C. and 592 milliliters of ethanol was added dropwise over 0.5 hour while maintaining the internal temperature at 60°-65° C. The mixture was then stirred at 60°-65° C. for 0.5 to 1 hour and then slowly allowed to cool to 20°-25° C. over 15 hours.

The product was isolated by filtration and the cake sequentially washed with three 100 milliliter portions of 85:15 (v/v) ethanol/water, one 100 milliliter portion of 90:10 (v/v) ethanol/water, two 100 milliliter portion of absolute ethanol, and finally three 150 milliliter portions of hexane. After completion of the washing, a stream of nitrogen was drawn through the cake for 15 hours to dry the product and to obtain 60.3 grams (not corrected for water content) of the desired product. The purity of the product was 93 percent.

Recrystallization 61 grams of crystallized Compound I monopotassium salt was added to a mixture of 366 milliliters of water and 366 milliliters of ethanol and the mixture heated at 75°-78° C. until all of the solid dissolved. Then while maintaining this temperature, 1098 milliliters of absolute ethanol was added gradually over a one hour period. After completion of the addition, the temperature of the solution was lowered to 70°-75° C. and then seeded with 1 gram of Compound I, monopotassium salt. The seeded mixture was slowly cooled to 20°-25° C. with slow stirring over a 15 hour period. The product was isolated by filtration through a medium porosity sintered-glass funnel and the cake sequentially washed with three 100 milliliter portions of 80:20 (v/v) ethanol/water, one 100 milliliter portion of 90:10 (v/v) ethanol/water, two 100 milliliter portions of absolute ethanol and finally three 150 milliliter portions of hexane. A stream of nitrogen was drawn through the cake for 15 hours to dry the product and obtain 43.0 g of Compound I as the potassium salt.

EXAMPLE Ia

Conversion of Monopotassium to a Monosodium Salt

A solution of 6.0 grams of Compound IB where M was potassium in 80:20 (v/v) water/ethanol (600 mL) was pumped through a 2.5×30 cm column packed with "AMBERCHROM" 161/cd resin at a rate of 20 mL/min. The column was then washed with two bed volumes (ca 300 ml) of 80:20 (v/v) water (0.1M $NaH_2PO_4$ to pH 4.5/ethanol and then two bed volumes of 80:20 (v/v) water/ethanol at a rate of 20 mL/min. The product was then eluted from the column with 20:80 (v/v) water/ethanol collecting 40 mL fractions.

The rich cuts (>0.5 g/L, determined by HPLC analysis, ca 1 bed volume) were combined and concentrated in vacuo (100 mBar, 40° C.) to remove the ethanol. The residual water was removed to obtain the mono-sodium salt of Compound IB in a yield of 5.8 grams (98 percent).

EXAMPLE II

The foregoing process may be employed with good results in the preparation of the representative compounds within the genus defined by Compound I having the substituents designated in the following table:

TABLE

| $R_1$ | $R_2$ | $R_3$ | $R_4$ | X | $X^1$ | Y | Z | R | SEQ ID NO. |
|---|---|---|---|---|---|---|---|---|---|
| OH | OH | OH | OH | H | OH | $CH_3$ | $CONH_2$ | $C_{17}H_{31}$ | 1 |
| OH | OH | OH | OH | $CH_3$ | OH | $CH_3$ | $CONH_2$ | $C_{15}H_{31}$ | 2 |
| OH | H | OH | OH | $CH_3$ | OH | $CH_3$ | $CONH_2$ | $C_{15}H_{31}$ | 3 |
| H | H | OH | H | $CH_3$ | OH | $CH_3$ | $CONH_2$ | $C_{15}H_{31}$ | 4 |

TABLE-continued

| R₁ | R₂ | R₃ | R₄ | X | X¹ | Y | Z | R | SEQ ID NO. |
|---|---|---|---|---|---|---|---|---|---|
| H | H | H | H | $CH_3$ | OH | $CH_3$ | $CONH_2$ | $C_{15}H_{31}$ | 5 |
| OH | OH | H | H | $CH_3$ | OH | $CH_3$ | $CONH_2$ | $C_{15}H_{31}$ | 6 |
| H | OH | H | OH | $CH_3$ | OH | $CH_3$ | $CONH_2$ | $C_{15}H_{31}$ | 7 |
| H | OH | H | OH | H | OH | $CH_3$ | $CONH_2$ | $C_{15}H_{31}$ | 8 |
| OH | OH | H | OH | H | OH | $CH_3$ | $CONH_2$ | $C_{15}H_{31}$ | 9 |
| OH | OH | OH | OH | OH | OH | $CH_3$ | $CONH_2$ | $C_{15}H_{31}$ | 10 |
| OH | OH | OH | OH | $CH_3$ | OH | $CH_3$ | $CH_3$ | $C_{17}H_{31}$ | 11 |
| OH | OH | OH | OH | $CH_3$ | OH | $CH_3$ | $CH_3$ | $C_{17}H_{35}$ | 11 |
| H | OH | OH | OH | $CH_3$ | OH | $CH_3$ | $CH_3$ | $C_{17}H_{35}$ | 12 |
| H | OH | H | H | $CH_3$ | OH | $CH_3$ | $CH_3$ | $C_{17}H_{35}$ | 13 |
| H | OH | OH | OH | H | OH | $CH_3$ | $CONH_2$ | $C_{15}H_{31}$ | 14 |
| H | OH | OH | OH | $CH_3$ | OH | $CH_3$ | $CONH_2$ | $C_{15}H_{31}$ | 15 |
| OH | OH | H | OH | $CH_3$ | OH | $CH_3$ | $CONH_2$ | $C_{15}H_{31}$ | 16 |
| OH | OH | OH | OH | $CH_3$ | OH | H | $CONH_2$ | $C_{15}H_{31}$ | 17 |

The usefulness of the phosphate derivatives may be seen in the following representative study on immunosuppressed rats for efficacy against *Pneumocystis carinii*.

Compound I as the free acid was used in the study. Sprague-Dawley rats (weighing approximately 250 grams) were immunosuppressed with dexasone in the drinking water (2.0 mg/L) and maintained on a low protein diet for five weeks to induce the development of pneumocystis pneumonia from a latent infection. Before drug treatment, two rats were sacrificed to confirm the presence of *Pneumocystis carinii* pneumonia (PCP); both rats were found to have infections. Six rats (weighing approximately 150 grams) were injected twice daily for four days intravenously (I.V.) via the tail vein with Compound I in 0.25 ml of vehicle (distilled water). A vehicle control was also carried out. All animals continued to receive dexasone in the drinking water and low protein diet during the treatment period. At the completion of the treatment, all animals were sacrificed, the lungs were removed and processed, and the extent of disease determined by microscopic analysis of stained slides. The results of this study showed Compound I was effective in eliminating *P. carinii* cysts in four days with an $ED_{90}$ of approximately 0.6 mg/kg.

In a similar experiment, except that the rats were injected intraperitoneally (I.P.) twice daily for four days, the animals were sacrificed, the lungs removed and processed, and the extent of disease determined by microscopic analysis of stained slides. The results showed that Compound I as the free acid was effective in eliminating *P. carinii* cysts in four days with an $ED_{90}$ of approximately 0.6 mg/kg.

The compound is also useful against Candida organisms. The property may be illustrated with minimum fungicidal concentration (MFC) determinations in a microbroth dilution assay carried out in a Yeast Nitrogen Base (Difco) medium with 1 percent dextrose (YNBD). In carrying out the assay, Compound I was solubilized in 10 percent dimethyl sulfoxide (DMSO) and diluted to 2560 μg/ml. The compound was then diluted to 256 μg/ml in YNBD. 0.15 ml of the suspension was dispensed to the top row of a 96-well plate (each well containing 0.15 ml of YNBD) resulting in a drug concentration of 128 μg/ml. Two-fold dilutions were then made from the top row to obtain final drug concentrations ranging from 128 to 0.06 μg/ml.

The yeast cultures, maintained on Sabouraud dextrose agar were transferred to YN broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 ml per well yielding a final inoculum per well of $1.5-7.5 \times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 μl samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot. The results are seen in the following table:

| FUNGI STRAIN NO. | MINI FUNGICIDAL CONCENTRATION μg/mL) |
|---|---|
| *C. albicans* | |
| MY 1055 | 2 |
| MY 1208 | 4 |
| MY 1028 | 4 |
| *C. tropicalis* | |
| MY 1012 | 1 |
| *C. parapsilosis* | |
| MY 1010 | 32 |

Preparation of the Starting Materials

The starting material, Compound A, may be prepared by inoculating agar slants of MF 5404 *Z. arboricola* ATCC 20957 in 54 milliliters of KF seed medium of the following composition: corn steep liquor, 5.0 g; tomato paste 40.0 g; oat flour 10.0 g; glucose, 10.0 g; trace elements, 10 ml, water 1000 ml, pH 6.8 where the trace elements are in a solution containing per liter of 0.6 $NH_4Cl$, $FeSO_4.7H_2O$, 1.0 g; $MnSO_4.4H_2O$, 1.0 g, $CuCl.2H_2O$, 0.025 g; $CaCl_2$; 0.1 g; $H_3BO_3$, 0.056 g; $(NH_4)_6Mo_7O_{24}.4H_2O$, 0.019 g and $ZnSO_4.7H_2O$, 0.2 g, and incubating the inoculated medium at 25° C. at 220 rpm for four days. Thereafter, a 20 milliliter sample may be taken and used to inoculate 500 milliliters of KF medium and the inoculated medium incubated at 25° C. for three days at 220 rpm. Four such inoculated and incubated media may be used to inoculate 180 liters of KF medium containing 2 mL/L polypropylene glycol P-2000 and the medium cultivated at 25° C., air flow of 90 liters/minute, a pressure of 0.7 kg/cm² gauge, and agitator speed of 200 rpm. A 25 liter of this cultivation sample then may be used to inoculate 475 liters of a medium of the following components per liter: D-mannitol, 40 g; NZ-Amine (type E; casein hydrolysate, Humko-Sheffield, Memphis, Tenn.), 33 g; Fidco-Yeast Extract, 10 g; ammonium sulfate, 5 g and monopotassium phosphate, 9 g and 2 ml of polypropylene glycol P-2000. The medium is then sterilized at 120° C. for 25 minutes and then cultivated for five days at 25° C., air flow of 250 liters/minute, a pressure of 0.7 kg/cm² gauge, and an agitator speed of 150 rpm. The pH is allowed to decrease from an initial value of 6.0 to 5.5 and then maintained at 5.5±0.4 for five days then harvested and isolated by a series of chromatographic separations.

Many of the starting material compounds are natural products obtained by the cultivation in nutrient media of certain fungal organisms. Other starting materials may be obtained by deacylation of the side chain of an appropriate natural product to obtain a nuclear compound which is then acylated with an acylating agent of the desired side chain.

A compound in which $R_1$, $R_2$, $R_3$ and $R_4$ and OH, X is H and $X^1$ is OH, Y is $CH_3$ and Z is —$CONH_2$ also may be obtained by cultivation of Zalerion arboricola ATCC 20957.

A compound in which $R_1$, $R_2$, $R_3$ and $R_4$ are OH, X is $CH_3$, $X^1$ is OH, Y is $CH_3$ and Z is —$CONH_2$ and R is 9,11-dimethyltridecyl may be obtained by the cultivation of Zalerion arboricola ATCC 20868 in nutrient medium and isolating by chromatographic separation as more fully described in U.S. Pat. No. 4,931,352.

Another compound is which Z is —$CONH_2$, $R_1$, $R_3$, $R_4$ are OH, $R_2$ is H, X is H or $CH_3$ and $X^1$ is methyl, Y is H may be obtained by the cultivation of Cryptosporiopsis species ATCC 20594 as taught in Annual Reports in Medicinal Chemistry, Vol. 19, p 131 (1984).

Certain other compounds in which Z is $CONH_2$ and R is of various groups may be prepared by deacylation of the side chain of a natural product with a microorganism of the family such as Pseudomondacea or Actinoplanaceae, isolating the deacylated cyclohexapeptide and thereafter acylating with an active acyl derivative. A representative procedure for obtaining the various semi-synthetic compounds with differing lipophilic side chains and the process for obtaining many of the compounds may be found in U.S. Pat. No. 4,304,716 for obtaining the nucleus and U.S. Pat. No. 4,289,120 for preparing derivatives utilizing the nucleus. Similarly, semi-synthetic compounds may be obtained where Z is H. Thus, a representative process for deacylation of various natural products in which Z is H, is found described in U.S. Pat. No. 4,293,482.

In a representative deacylation with a Pseudomonas species, a dimethyl sulfoxide solution of the substrate cyclohexapeptide natural product is added to stirred suspension of cells of a Pseudomonas species in a phosphate buffer of pH 6.5 and then cultivated in a nutrient medium at 37° C. for 18 hours where upon deacylation occurs. The deacylated product is recovered from the supernatant on centrifuging to separate the cells and after purification, acylated by reacting with an activated acid derivative such as acyl halides, pentachlorophenoxides, alkylsulfonates or arylsulfonates at ambient temperature for 15 to 20 hours and thereafter purifying by conventional procedures.

Natural products which were of the structure where Z is H are known as echinocandins, aculiacins, mulundocandin, and variously identified by letter and number codes may be obtained by the cultivation of an Aspergillus organism. Thus, the echinocandins may be produced by Aspergillus rugulosus and the aculeacins by Aspergillus aculeatus and other echinocandin type compounds by Asp. niger, Asp. nidulans and the like.

A compound in which X and $X^1$ are both OH may be obtained by cultivating Z. arboricola ATCC 74030 in a nutrient medium for 3 to 30 days and there recovering the product in a conventional manner.

A compound in which $R_1$ and $R_3$ are H, with various other substituents may be prepared from the corresponding natural product or semi-synthetic compound in which $R_1$ and $R_3$ are OH by reacting the latter compound with sodium cyanoborohydride in trifluoroacetic acid with cooling and stirring under nitrogen atmosphere at 0° C. and thereafter completing the reaction at ambient temperature.

The product may be recovered by vaporizing the trifluoroacetic acid, dissolving the residue in methanol, adjusting the pH to about 8 and pouring it into water to obtain the product as precipitate which may be further purified by HPLC.

Compound in which $R_1$ is OH and $R_3$ is H may be prepared in a similar manner, except that the compound is in solution in a solvent such as glacial acetic acid or methylene dichloride before the reduction is carried out.

Compound in which $R_1$ is H and $R_3$ is OH may be prepared form the corresponding natural product or semi-synthetic compound in which $R_1$ and $R_3$ are OH by reacting a solution of the latter compound in trifluoroacetic acid with triacetoxyborohydride and stirring in a portionwise manner. After completion of the reaction, the volatiles may be removed under reduced pressure and the residue purified by preparative HPLC.

What is claimed is:

1. A method for producing a phosphate ester compound of a cyclohexapeptide of the formula

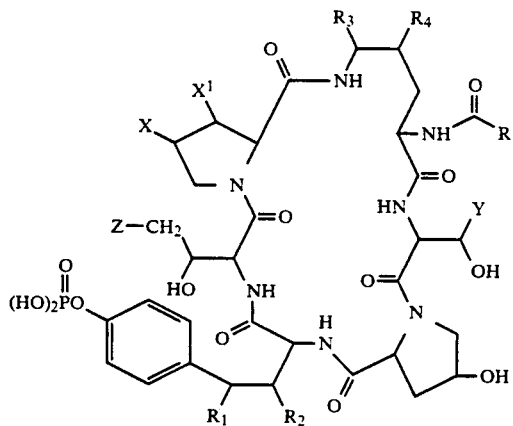

which comprises
(1) phosphorylating a cyclohexapeptide of the formula

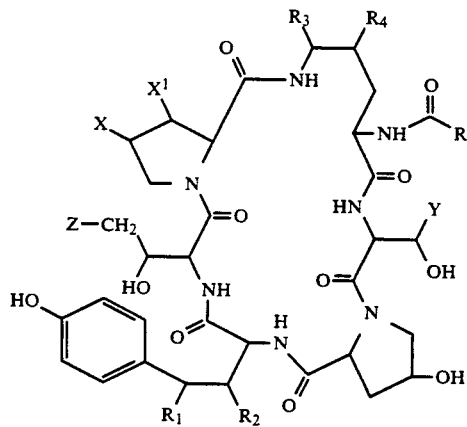

by mixing together said cyclohexapeptide with tetrabenzyl pyrophosphate in the presence of lithium hydroxide while the temperature is maintained in the range of about $-13°$ to $-17°$ C. to obtain a dibenzyl phosphate of said cyclohexapeptide having the formula

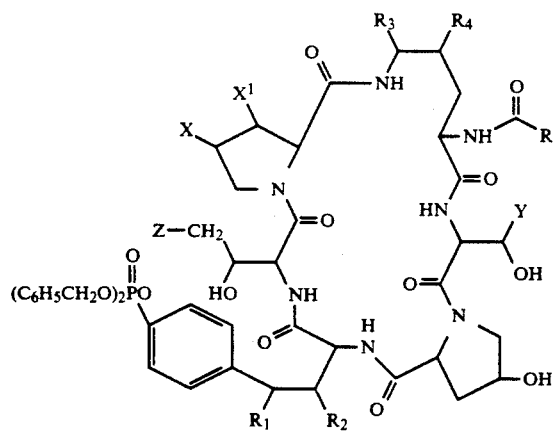

wherein in the foregoing formulas

R is $C_{13}$–$C_{17}$ alkyl, $C_{13}$–$C_{17}$ alkenyl, $C_{13}$–$C_{17}$ alkynyl, phenyl and phenyl substituted with $C_1$–$C_{10}$ alkyl, $C_1$–$C_{10}$ alkoxy, $C_1$–$C_{10}$ alkylthio or $C_1$–$C_{10}$ alkylamino;

$R_1$, $R_2$, $R_3$ and $R_4$ are independently H or OH,

X is H, OH or $CH_3$, $X^1$ is H or OH,

Y is H or $CH_3$, and

Z is H or $-CONH_2$ provided that at least one of X and $X^1$ is OH.

2. A method for producing a phosphate ester compound of a cyclohexapeptide of the formula

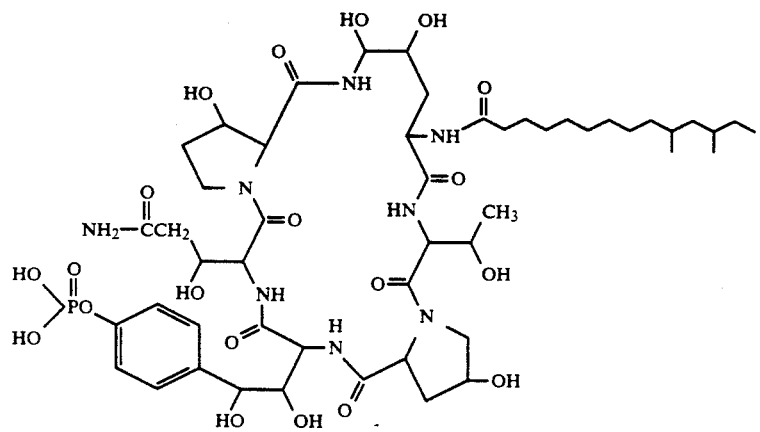

which comprises (1) phosphorylating a cyclohexapeptide of the formula

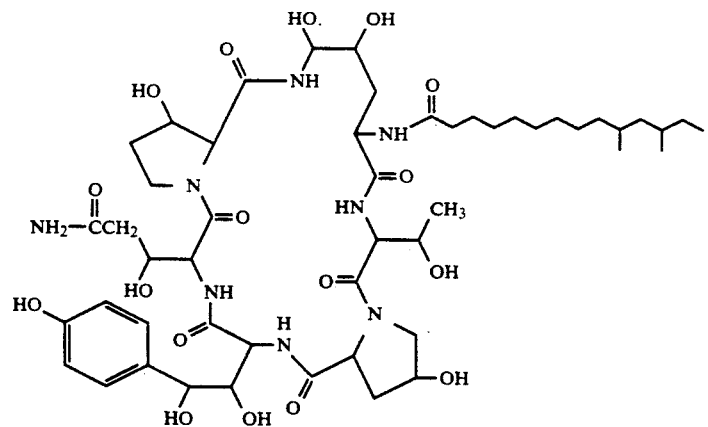

and (2) debenzylating the dibenzyl phosphate ester of the cyclohexapeptide thus obtained by hydrogenolysis on Pd/C by mixing together said cyclohexapeptide with tetrabenzyl pyrophosphate in the presence of lithium hydroxide while the temperature is maintained from about $-13°$ to $-17°$ C. to obtain a dibenzyl phosphate of said cyclohexapeptide having the formula

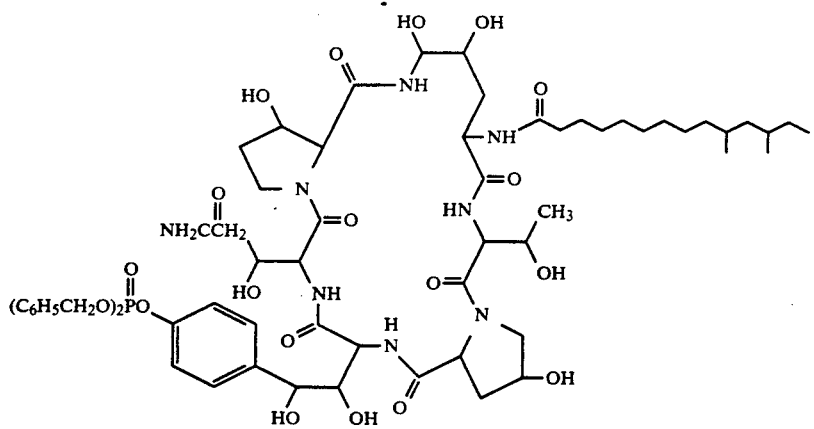

(2) debenzylating the deibenzyl phosphate ester of the cyclohexapeptide thus obtained by hydrogenolysis on Pd/C.

3. A process for facilely producing a compound of the formula

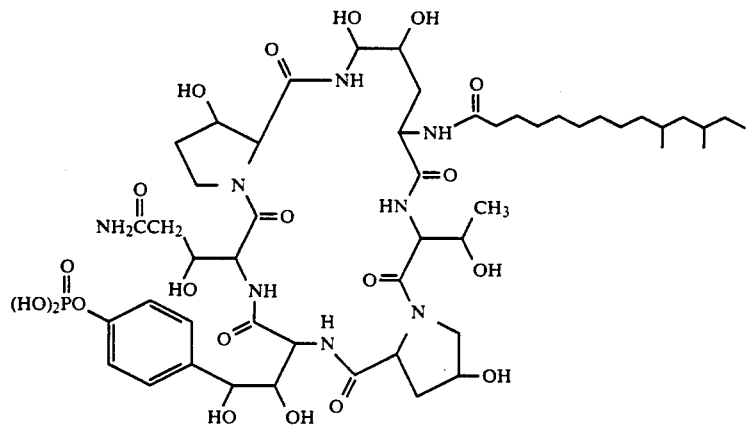

which comprises
(1) phosphorylating by
  (a) adding a compound of the formula

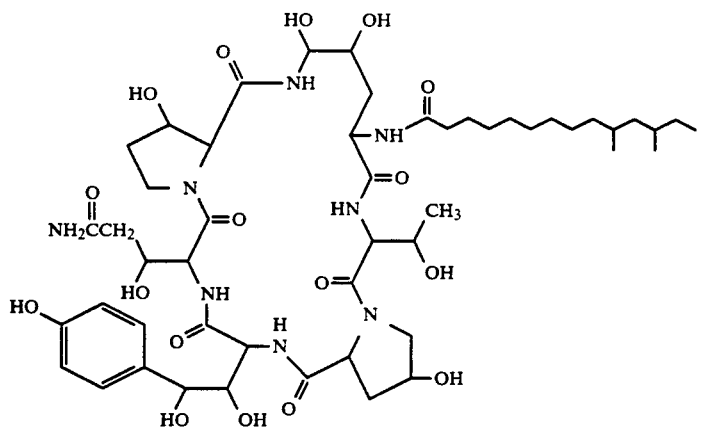

and dimethylformamide to a dimethylformamide solution of tetrabenzyl pyrophosphate and stirring to complete dissolution,
  (b) adding an aqueous solution of lithium hydroxide thereto with stirring at a rate to maintain the internal temperature at about −15° C., and continuing the stirring until the reaction is complete;
(2) changing solvent medium
  (a) by acidifying the phosphorylating mixture and adding said mixture into 50:50 (v/v) ethanol/water and passing the resulting solution through a non-functionalized column to adsorb the dibenzyl phosphate ester thereon,
  (b) washing the column with 50:50 ethanol/water, and
  (c) eluting the dibenzyl phosphate ester with 90:10 ethanol/water;

(3) hydrogenolysing the benzyl ester group by
  (a) contacting the eluate with hydrogen in the presence of palladium on carbon catalyst, and
  (b) filtering to remove the catalyst.
4. A process according to claim 3 which includes the further step of directly converting the acid product in the filtrate of the hydrogenolysis to produce a crystalline mono salt.

* * * * *

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
( A ) LENGTH: 6
( B ) TYPE: AMINO ACID
( C ) STRANDEDNESS: NA
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 1:

Xaa  Thr  Xaa  Xaa  Xaa  Xaa
    1                        5

( 2 ) INFORMATION FOR SEQ ID NO: 2:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 2:

Xaa  Thr  Xaa  Xaa  Xaa  Xaa
    1                        5

( 2 ) INFORMATION FOR SEQ ID NO: 3:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 3:

Xaa  Thr  Xaa  Xaa  Xaa  Xaa
    1                        5

( 2 ) INFORMATION FOR SEQ ID NO: 4:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 4:

Xaa  Thr  Xaa  Xaa  Xaa  Xaa
    1                        5

( 2 ) INFORMATION FOR SEQ ID NO: 5:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 5:

Xaa  Thr  Xaa  Xaa  Xaa  Xaa
    1                        5

( 2 ) INFORMATION FOR SEQ ID NO: 6:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 6:

Xaa  Thr  Xaa  Xaa  Xaa  Xaa
    1                          5

( 2 ) INFORMATION FOR SEQ ID NO: 7:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 7:

Xaa  Thr  Xaa  Xaa  Xaa  Xaa
    1                          5

( 2 ) INFORMATION FOR SEQ ID NO: 8:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 8:

Xaa  Thr  Xaa  Xaa  Xaa  Xaa
    1                          5

( 2 ) INFORMATION FOR SEQ ID NO: 9:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 9:

Xaa  Thr  Xaa  Xaa  Xaa  Xaa
    1                          5

( 2 ) INFORMATION FOR SEQ ID NO: 10:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 10:

Xaa  Thr  Xaa  Xaa  Thr  Xaa
    1                          5

( 2 ) INFORMATION FOR SEQ ID NO: 11:

( i ) SEQUENCE CHARACTERISTICS:
        ( A ) LENGTH: 6
        ( B ) TYPE: AMINO ACID (C) STRANDEDNESS: NA
(D) TOPOLOGY: CIRCULAR (i i) MOLECULE TYPE:
(A) DESCRIPTION: PEPTIDE (x i) SEQUENCE DESCRIPTION: SEQ ID NO: 11:

Xaa Thr Xaa Xaa Thr Xaa
 1                    5

(2) INFORMATION FOR SEQ ID NO: 12:

(i) SEQUENCE CHARACTERISTICS:
(A) LENGTH: 6
(B) TYPE: AMINO ACID
(C) STRANDEDNESS: NA
(D) TOPOLOGY: CIRCULAR (i i) MOLECULE TYPE:
(A) DESCRIPTION: PEPTIDE (x i) SEQUENCE DESCRIPTION: SEQ ID NO: 12:

Xaa Thr Xaa Xaa Thr Xaa
 1                    5

(2) INFORMATION FOR SEQ ID NO: 13:

(i) SEQUENCE CHARACTERISTICS:
(A) LENGTH: 6
(B) TYPE: AMINO ACID
(C) STRANDEDNESS: NA
(D) TOPOLOGY: CIRCULAR (i i) MOLECULE TYPE:
(A) DESCRIPTION: PEPTIDE (x i) SEQUENCE DESCRIPTION: SEQ ID NO: 13:

Xaa Thr Xaa Xaa Thr Xaa
 1                    5

(2) INFORMATION FOR SEQ ID NO: 14:

(i) SEQUENCE CHARACTERISTICS:
(A) LENGTH: 6
(B) TYPE: AMINO ACID
(C) STRANDEDNESS: NA
(D) TOPOLOGY: CIRCULAR (i i) MOLECULE TYPE:
(A) DESCRIPTION: PEPTIDE (x i) SEQUENCE DESCRIPTION: SEQ ID NO: 14:

Xaa Thr Xaa Xaa Xaa Xaa
 1                    5

(2) INFORMATION FOR SEQ ID NO: 15:

(i) SEQUENCE CHARACTERISTICS:
(A) LENGTH: 6
(B) TYPE: AMINO ACID
(C) STRANDEDNESS: NA
(D) TOPOLOGY: CIRCULAR (i i) MOLECULE TYPE:
(A) DESCRIPTION: PEPTIDE (x i) SEQUENCE DESCRIPTION: SEQ ID NO: 15:

Xaa Thr Xaa Xaa Xaa Xaa
 1                    5

(2) INFORMATION FOR SEQ ID NO: 16:

(i) SEQUENCE CHARACTERISTICS:
  (A) LENGTH: 6
  (B) TYPE: AMINO ACID
  (C) STRANDEDNESS: NA
  (D) TOPOLOGY: CIRCULAR (ii) MOLECULE TYPE:
  (A) DESCRIPTION: PEPTIDE (xi) SEQUENCE DESCRIPTION: SEQ ID NO: 16:

```
Xaa  Thr  Xaa  Xaa  Xaa  Xaa
 1                 5
```

(2) INFORMATION FOR SEQ ID NO: 17:

(i) SEQUENCE CHARACTERISTICS:
  (A) LENGTH: 6
  (B) TYPE: AMINO ACID
  (C) STRANDEDNESS: NA
  (D) TOPOLOGY: CIRCULAR (ii) MOLECULE TYPE:
  (A) DESCRIPTION: PEPTIDE (xi) SEQUENCE DESCRIPTION: SEQ ID NO: 17:

```
Xaa  Ser  Xaa  Xaa  Xaa  Xaa
 1                 5
```